(12) United States Patent
Pisciotta

(10) Patent No.: US 6,753,180 B1
(45) Date of Patent: Jun. 22, 2004

(54) CLONAL REPLICATION SYSTEM

(75) Inventor: John M. Pisciotta, Tampa, FL (US)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 10/248,354

(22) Filed: Jan. 13, 2003

Related U.S. Application Data

(60) Provisional application No. 60/319,059, filed on Jan. 11, 2002.

(51) Int. Cl.[7] .................................................. C12M 1/26
(52) U.S. Cl. .................................. 435/309.4; 435/309.1
(58) Field of Search ............................ 435/309.1, 309.4

(56) References Cited

U.S. PATENT DOCUMENTS

| | | |
|---|---|---|
| 3,932,220 A | 1/1976 | Liotta |
| 4,368,272 A | 1/1983 | Kashket |
| 4,397,955 A | 8/1983 | Entis et al. |
| 4,480,031 A | 10/1984 | Shaw |
| 4,591,567 A | 5/1986 | Britten et al. |
| 4,634,676 A | 1/1987 | Sapatino |
| 4,659,672 A | 4/1987 | Provonchee et al. |
| 4,659,673 A | 4/1987 | Brown |
| 4,717,667 A | 1/1988 | Provonchee |
| 5,061,621 A | 10/1991 | Perlman |
| 5,691,195 A | 11/1997 | Doleans et al. |

OTHER PUBLICATIONS

Replica–Plating Tool—www.belart.com/catalog/lifescience/205–replica–plate–tool.html Dec. 5, 2000.
Scienceware* Replica–Plating Tool—www.fishersci.com Dec. 5, 2000.

*Primary Examiner*—David A. Redding
(74) *Attorney, Agent, or Firm*—Molly L. Sauter; Smith & Hopen, P.A.

(57) ABSTRACT

The present invention provides for a colony replicator transfer disk, a first side having a colony collecting substrate and a second side having a mechanism to attach the transfer disk to a stamping base. A substantially fluid impervious layer exists between the side and the second side of the transfer disk.

9 Claims, 2 Drawing Sheets

FIG. 1 – Prior Art

CLONAL REPLICATION SYSTEM

CROSS REFERENCE TO RELATED APPLICATION

This application claims priority from U.S. provisional application 60/319,059. "Clonal Replication System", filed Jan. 11, 2002.

BACKGROUND OF INVENTION

Velvet based colony replication has been widely used for at least 50 years. Early velvet replicators were simple devices, no more than a round block used to support a sterile sheet of fabric via rubber band or hoop. In the early 1980's Richard Provanchee of Philadelphia recognized some of the problems with traditional velvet replication and developed a replicator which employed a soft, compliant foam base to support the sterile transfer material which was not velvet but rather an open cell, flexible and water absorbent foam. This transfer surface was affixed to the flexible base via an adhesive.

In 1989 David Perlman developed a fabric-based replicator that did not employ a foam base but possessed so-called "bumper guards". These were apparently a slightly raised margin which allowed the device to accommodate the raised meniscus of agar plates. Perlman's transfer surface was "fixedly bonded" to the replicator via an adhesive tab. He also included a marking element which indicated the orientation of replicated plates by indenting a portion of each plates agar surface.

Another problem with other replicators lies in the use of adhesives or rubber bands to affix the transfer materiel. Adhesives are messy and loose their "Stick" over time. Rubber bands and loops can be difficult to position and must be passed over the sterile velvet surface without contacting and thereby contaminating it.

The transfer step is a time consuming bottleneck that severely limits the number of plates processed per day. To speed things up an old microbiological technique known as velvet plating may be employed. For this a cylindrical block of wood or plastic is placed on top of an inverted square of sterilized velvet. The four corners of overlapping velvet are next drawn up against the sides of the cylinder and a rubber band is drawn over these so as to hold the velvet in place. With the sterilized velvet in this way attached to the supporting block one can quickly lift all colonies from an incubated plate and transfer them to the surface of a new recipient plate or series of plates.

This sounds simple enough in theory, but in practice one soon finds that attempting to hold all four corners of velvet in position while trying to slip a rubber band over each while not touching and thereby contaminating the sterile velvet is easier said than done. Indeed, any touching of the velvet whatsoever may introduce contaminants. In addition to inconvenience and frustration other more serious problems inherent in the old method exist.

The first of these problems is caused by the peripheral wrinkles and overlapping foldings of fabric that can arise when one forces a square piece of loose cloth to conform to the form of a circle. This peripheral wrinkling causes what may be thought of as "contact shadows". The piled up fabric of the wrinkle prevents adjacent, lower-lying velvet from contacting the agar. Thus the fabric in this shadow neither lifts colonies from the template nor transfers to the recipient plate. Although it is possible to prevent this problem via careful attention to detail while positioning the rubber band this takes added time, skill and again can increase the risk of surface contamination via excessive manipulation.

The second problem was a transfer failure of colonies. The root of this problem rests in the use of a flat, rigid cylinder base against which the velvet square is bound. If the surface of the Petri dish agar were as geometrically correct as the block base there would be no problem, however, due to the manner in which Petri plates are prepared this is not the case.

Agar media is prepared much like gelatin: a powder is added to water, it is dissolved, then autoclaved (heated at high temperature to sterilize) and poured into a mold. The difference is that in microbiology the mold is a flat and shallow Petri dish. As the added small volume of hot liquid agar is quickly swirled in order to fully cover the bottom of the plate it rapidly cools and solidifies. The result: the peripheral edge of agar in a Petri plate forms a raised lip against the wall of the plate.

When the replicator is subsequently pressed down on such a plate, the rigid velvet covered base presses down first on the higher agar of the peripheral lip region. Only with increased pressure is this agar lip region pressed down sufficiently so as to allow the centrally located colonies to be contacted by the sterile velvet This crushing of the peripheral agar to get at the central colonies can ruin any chance of getting a successful lift and transfer and often may destroy the template plate as well. This is because even if the crushed agar is not torn up as the velvet is removed, water forced from the agar matrix while under pressure, facilitates the mixing and cross-contamination of the minute bacterial cells which make up each colony.

Furthermore, this causes contamination of the replicator itself as the microscopic cells pass through the relatively loose grid of interwoven Velvet fibers. Replicator contamination makes It necessary to ethanol sterilize the device base prior to attachment of each new piece of velvet. Otherwise residual cells on the device can pass back through the fabric and cross-contaminate new plates.

The need for repeated sterilization of the device between each use is tedious and substantially adds to the time required to replicate multiple plates. Furthermore, one must ensure that all ethanol has evaporated since any residual disinfectant might kill the cells one is attempting to replicate: thereby leading to false negative results.

SUMMARY OF INVENTION

In a preferred embodiment of the present invention, a clonal replicator transfer disk is provided for transferring colonies from one agar surface to another. The transfer disk comprises a first side having a colony collecting substrate and a second side having an attachment means adapted to releasably engage a stamping base, the first side and the second side sandwiching a substantially fluid impervious layer.

In another preferred embodiment, the clonal reclicator transfer disk is substantially the shape of a Petri dish and the stamping base is contoured to mimic the shape of a prepared agar surface.

In yet another embodiment, the clonal replicator transfer disk comprises a marginal pull tab to assist in the removal of the transfer disk from the stamping base without the risk of contamination.

In another embodiment, the clonal replicator transfer is attached to the stamping pad with VELCRO.

In an additional embodiment, the stamping base further comprises an orientation marker to assist it proper orientation of the colonies on the agar surface.

In yet another embodiment of the clonal replicator transfer disk, the substantially fluid Impervious layer also exhibits resistant to high temperature to allow for autoclaving sterilization.

In an additional embodiment, the colony collecting substrate of the clonal replicator transfer disk is velvet.

In yet another embodiment, the colony collecting substrate of the clonal replicator transfer disk is suede.

The invention accordingly comprises the features of construction, combination of elements, and arrangement of parts that will be exemplified in the description set forth hereinafter and the scope of the invention will be indicated in the claims.

Other aspects and advantages of the present invention can be seen upon review of the figures, the detailed description, and the claims which follow.

BRIEF DESCRIPTION OF THE DRAWING

More specifically, FIG. 2(a) is an illustration of the replicator base and FIG. 2(b) is an illustration of the transfer disk of the present invention.

DETAILED DESCRIPTION

Figure 1:
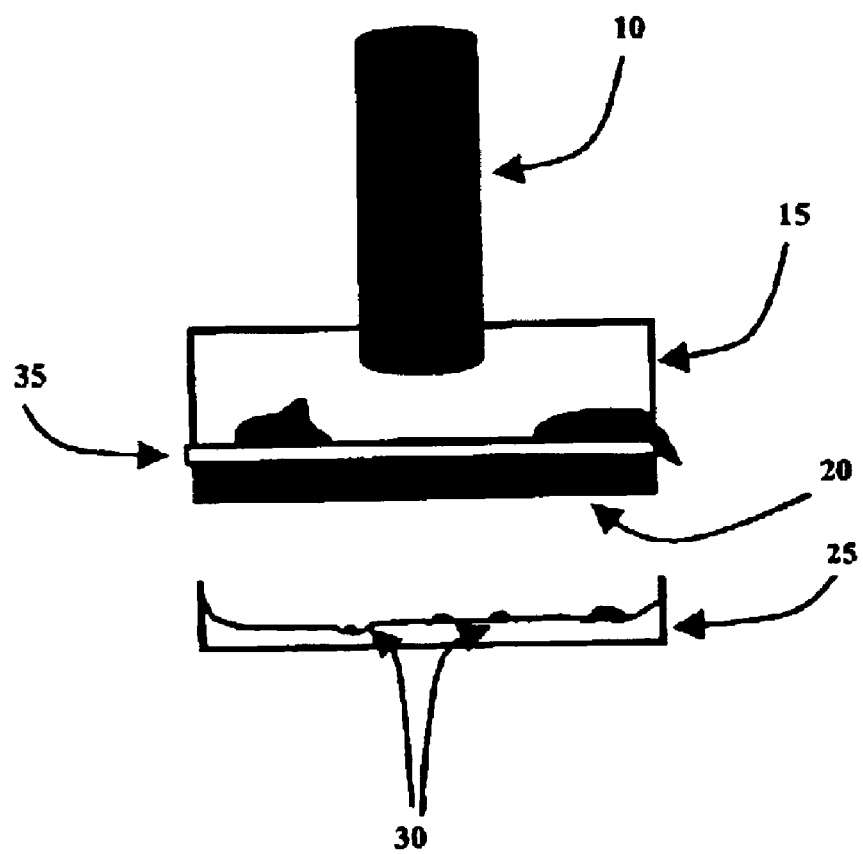
FIG. 1 is an illustration of the prior art method of velvet plating.

FIG. 1 illustrates a prior art apparatus used for colony transfer. In this prior art example, an inverted square of sterilized velvet 20 is secured by a rubberband 35 to a cylindrical block of wood or plastic 75 having a grip 70. With the steralized velvet attached to the supporting block in this manner, one can quickly lift colonies 30 from an incubated plate 25 and transfer them to the surface of a new recipient plate. The deficiencies with this method have been previously described.

Figure 2:
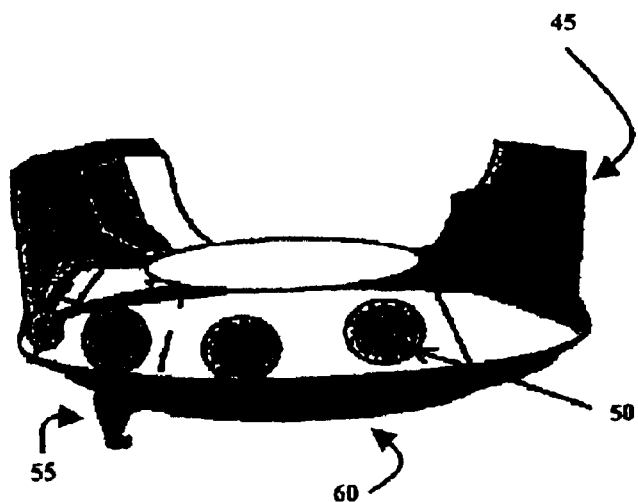
FIG. 2 is an illustration of an embodiment of the present invention.
Figure 2:
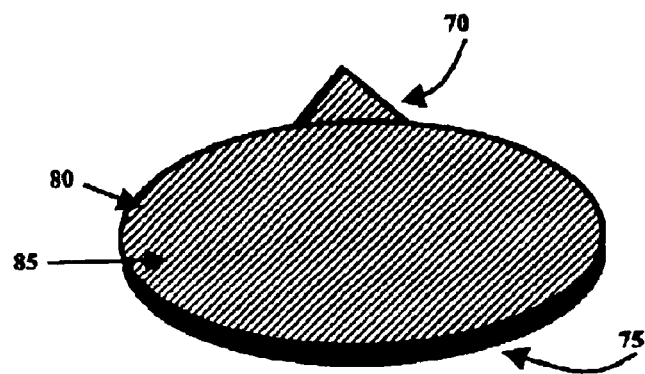

As illustrated in FIG. 2(a) and FIG. 2(b), the present invention provides a novel and non-obvious colony replicator. FIG. 2(a) details the colony replicator base 40 which comprises at least one support member 45 and a distal end adapted to secure the transfer disk 60. In a preferred embodiment the replicator's distal end is covered with fine VELCRO "hooks" which allows the user to rapidly and securely affix each pre-sterilized transfer disk without having to handle it in anyway. This eliminates the need for rubber bands and avoids the risk of inadvertent contamination of the transfer surface by the user FIG. 2(b) details the transfer disk 65 of the present invention. Rather than rough-cut velvet squares, the invention employs fine velveteen or suede transfer disks 65 which are custom cut to the 4¼" diameter of the standard Petri dish. Each transfer disk is equipped with a marginal pull tab 70. The course, non-contact surface of each transfer disk is coated with a high temperature resistant, waterproof silicon sealant 80.

Large numbers of transfer disks are easily produced by first evenly applying the sealant backing 80 to sheets of velvet or suede 75. Before the sealant fixes, the VELCRO "fuzz" 85 is evenly applied. Once the silicon dries, the even layer of "fuzz" is permanently affixed. Multiple identical transfer disks can then be rapidly cut from this sheet using a 4¼" diameter cutting guide (plus marginal pull tab). Transfer disks are then stacked, contact face down on aluminum foil, wrapped and autoclave sterilized.

The silicon backing 80 serves a number of non-obvious and complementary functions aside from simply securing the VELCRO fuzz 85. For instance, the uniform silicon backing provides a level of flexible support which prevents folding and wrinkling of the transfer disks. Since wrinkling is avoided one need no longer waste time and risk contamination by manipulating wrinkled velvet into position in order to ensure uniform replication.

Furthermore, each siliconized transfer disk is now transformed from a loose sieve into an impervious barrier through which bacterial cells and contaminants cannot pass. This is of primary importance for it eliminates trans-fabric cross-contamination of both replicator and plates. By so preventing the exchange of contaminants through the transfer material, the need for ethanol sterilization of the replicator prior to each use is obviated.

In addition, used transfer disks may be sterilized, washed, and reused many times without any loss of replication fidelity since the silicon sealant also secures the marginal velvet fibers to the woven grid of the fabric; thereby preventing them from falling out. This is in contrast to regular velvet squares which rapidly fray and loose their fibers over time as nothing secures each fiber to the fabric. Because these new. transfer disks do not go threadbare with use, replacement costs are minimized.

Following use transfer disks are easily removed with a minimum of handling via the uncontaminated pull tab 70. This reduces risk to the operator when pathogens are involved. By using a VELCRO "hooks" covered washing board and a fine brush, transfer disks can be easily washed.

The replicator body 40 developed features a smaller more ergodynamic concave design which allows it to be used in an inverted manner either supported on the knee or the bench top. Finger pads 50 may be included for extra support. This frees both hands allowing for rapid use. Furthermore, since Petri dishes, as well as most microbial growth agars, are transparent, inverted replication also allows the user to verify that the entire surface of the plate (including "sinkers") has been contacted.

This device is well equipped to contact agar digesting "sinkers" for the layer of silicon, VELCRO fuzz and VELCRO hooks developed between the replicator's base and the sterile transfer surface allows the fabric to conform to the unique irregularities of each plate without placing uneven pressure on raised areas. This even dispersion of force prevents crushing with pressing of water from the agar matrix. Consequently. plates are preserved and mixing of isolated colonies is prevented.

By using a hook and loop VELCRO system secured via the silicon these problems are avoided with a rapid fire change out system. Furthermore, this system synergistically addresses the need to conform to each plate's surface and contact sinkers. It does so in a unique manner that is not anticipated by the fairly obvious foam base method used in prior art methods. Other needs such as fabric fraying, wrinkling and user risk are also addressed by the unique construction of this device.

By using autoclave resistant silicon as a backing agent it was discovered that not only is velvet wrinkling prevented but the imparted impermeability of the treated material solves another problem by preventing transmission of bacterial cells through the velvet to the device base and vice versa. Consequently, contamination of the device base, inherent in currently marketed products, is prevented. Furthermore, the two-way impenetrability of the treated velveteen synergistically obviates the need for time-consuming and potentially dangerous ethanol or bleach-based disinfection of the device base between transfers.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

Is also to be understood that the following claims are intended to cover all of the generic and specific features of the invention herein described, and all statements of the scope of the invention which, as a matter of language, might be said to fall therebetween.

Now that the invention has been described
What is claimed is:

1. A clonal replicator comprising:
   a stamping base; and
   a transfer disk further comprising a first side having a colony collecting substrate and a second side having an attachment means adapted to releasably engage the stamping base, the first side and the second side sandwiching a substantially fluid impervious layer.

2. The clonal replicator of claim 1, wherein the transfer disk is substantially the shape of a Petri dish.

3. The clonal replicator of claim 1, further comprising a marginal pull tab adapted to assist in the removal of the transfer disk from the stamping base.

4. The clonal replicator of claim 1, wherein the attachment means is VELCRO loops and the stamping base is adapted with VELCRO hooks to releasably receive the transfer disk.

5. The clonal replicator of claim 1, wherein the stamping base further comprises an orientation marker.

6. The clonal replicator of claim 1, wherein the stamping base is contoured to substantially mimic the shape of a prepared agar surface.

7. The clonal replicator of claim 1, wherein the substantially fluid impervious layer is high-temperature resistant.

8. The clonal replicator of claim 1, wherein the colony collecting substrate is velvet.

9. The clonal replicator of claim 1, wherein the colony collecting substrate is suede.

* * * * *